United States Patent
Mesa Pardillo et al.

(10) Patent No.: US 11,766,462 B2
(45) Date of Patent: Sep. 26, 2023

(54) GANGLIOSIDE GM3-CONTAINING NANOPARTICLES AS IMMUNOMODULATORS

(71) Applicant: Centro de Inmunología Molecular, Havana (CU)

(72) Inventors: Circe Mesa Pardillo, Havana (CU); Liliana Oliver Ríos, Havana (CU); Rydell Alvarez Arzola, Havana (CU); Vladimir Peña Sánchez, Havana (CU); Luis Enrique Fernández Molina, Havana (CU); Anet Valdés Zayas, Havana (CU); Maura Lisett Rábade Chediak, Havana (CU); Lena Aguiar García, Prov. Artemisa (CU); Lourdes Hernández de La Rosa, Havana (CU); Audry Fernández Gómez, Havana (CU); Leslie Pérez Ruíz, Plaza de la Revolución (CU); Camilo Rodríguez Rodríguez, Plaza de la Revolución (CU); Elias Antonio Gracia Medina, Havana (CU); María Caridad Rubio Hernández, Havana (CU); Orlando Valdés Guerrero, Havana (CU); Idelmis Curbelo Haredia, Havana (CU)

(73) Assignee: Centro de Inmunología Molecular, Havana (CU)

( * ) Notice: Subject to any disclaimer, the term of this patent is extended or adjusted under 35 U.S.C. 154(b) by 380 days.

(21) Appl. No.: 16/957,597

(22) PCT Filed: Dec. 17, 2018

(86) PCT No.: PCT/CU2018/050005
§ 371 (c)(1),
(2) Date: Jun. 24, 2020

(87) PCT Pub. No.: WO2019/129313
PCT Pub. Date: Jul. 4, 2019

(65) Prior Publication Data
US 2020/0330527 A1    Oct. 22, 2020

(30) Foreign Application Priority Data
Dec. 27, 2017  (CU) .................................. 20170173

(51) Int. Cl.
*A61K 35/74* (2015.01)
*A61P 35/00* (2006.01)
*A61K 9/51* (2006.01)

(52) U.S. Cl.
CPC .............. *A61K 35/74* (2013.01); *A61P 35/00* (2018.01); *A61K 9/51* (2013.01)

(58) Field of Classification Search
CPC ............ A61K 35/74; A61K 9/51; A61P 35/00
See application file for complete search history.

(56) References Cited

U.S. PATENT DOCUMENTS

| | | | |
|---|---|---|---|
| 6,149,921 A | 11/2000 | Rodriguez et al. | |
| 7,776,342 B2* | 8/2010 | Fernandez Molina | A61K 39/001103 424/277.1 |
| 8,591,917 B2 | 11/2013 | Molina et al. | |
| 2020/0330527 A1 | 10/2020 | Mesa Pardillo et al. | |

FOREIGN PATENT DOCUMENTS

EP      1356822 B1    10/2010
WO   WO-2019/129313 A1   7/2019

OTHER PUBLICATIONS

BioCubaFarma: accelerating the development of cancer immunotherapies, Biopharma Deal Makers (2018).
Bronte et al., "Recommendations for myeloid-derived suppressor cell nomenclature and characterization standards," Nature Communications, 7: Article 12150 (2016).
Carr et al., "Immunotherapy of Advanced Breast Cancer With a Heterophilic Ganglioside (NeuGcGM3) Cancer Vaccine," Journal of Clinical Oncology, 21(6): 1015-1021 (2003).
Condamine et al., "Molecular mechanisms regulating myeloid-derived suppressor cell differentiation and function," Trends in Immunology, 32(1): 19-25 (2011).
Estevez et al., "Enhancement of the immune response to poorly immunogenic gangliosides after incorporation into very small size proteoliposomes (VSSP)," Vaccine, 18: 190-197 (2000).
Fernandez et al., "Inhibition of Tumor-Induced Myeloid-Derived Suppressor Cell Function by a Nanoparticulated Adjuvant," The Journal of Immunology, 186: 264-274 (2011).
Fernandez et al., "Very small size proteoliposomes abrogate crosspresentation of tumor antigens by myeloid-derived suppressor cells and induce their differentiation to dendritic cells," Journal for ImmunoTherapy of Cancer, 2(5): 1-16 (2014).

(Continued)

*Primary Examiner* — Robert A Zeman
(74) *Attorney, Agent, or Firm* — Foley Hoag LLP; Philip S. Choi; David Shore

(57) ABSTRACT

The present invention describes a pharmaceutical composition whose active ingredient includes conjugates of membrane vesicles of *Neisseria meningitidis* and the GM3 ganglioside in a conjugation ratio in excess of proteins, has particular characteristics of size, surface charge and a morphology associated with nano-particulate systems that give it advantageous properties as an immunomodulator, because it induces a convenient and significant reduction of myeloid-derived suppressor cells that has an impact on the response of lymphocytes and on the survival of patients with tumors. The invention further discloses the use of the pharmaceutical composition disclosed in the treatment of cancer, particularly those cancers where the myeloid-derived suppressor cells (MDSCs) are high; as well as a method of treatment with said composition in cancer patients and a method to select those who will receive said treatment.

6 Claims, 4 Drawing Sheets

(56) References Cited

OTHER PUBLICATIONS

International Search Report and Written Opinion for International Application No. PCT/CU2018/050005 dated Apr. 25, 2019.
Khong et al., "Adjuvants for peptide-based cancer vaccines," Journal for ImmunoTherapy of Cancer, 4(56): 1-11 (2016).
Ko et al., "Sunitinib Mediates Reversal of Myeloid-Derived Suppressor Cell Accumulation in Renal Cell Carcinoma Patients," Cancer Therapy: Clinical, 15(6): 2148-2157 (2009).
Malmberg., "Effective immunotherapy against cancer," Cancer Immunology ImmunoTherapy, 53: 879-892 (2004).
Mantovani et al., "Macrophages, innate immunity and cancer: balance, tolerance, and diversity," Current Opinion in Immunology, 22: 231-237 (2010).
Mulens et al., "Immunogenicity and safety of a NeuGcGM3 based cancer vaccine: Results from a controlled study in metastatic breast cancer patients," Human Vaccines, 6(9): 736-744 (2010).
Najjar et al., "Clinical Perspectives on Targeting of Myeloid Derived Suppressor Cells in the Treatment of Cancer," Frontiers in Oncology, 3(49): 1-24 (2013).
Oliver et al., "Very small size proteoliposomes derived from Neisseria meningitidis: An effective adjuvant for antigen-specific cytotoxic T lymphocyte response stimulation under leukopenic conditions," Vaccine, 30: 2963-2972 (2012).
Serda., "Particle platforms for cancer immunotherapy," International Journal of Nanomedicine, 2013(8): 1683-1696 (2013).
Shipp et al., "A clinical and biological perspective of human myeloid-derived suppressor cells in cancer," Cellular and Molecular Life Sciences, 73: 4043-4061 (2016).
Wilkerson et al., "Nanoparticle Systems Modulating Myeloid-Derived Suppressor Cells for Cancer Immunotherapy," Current Topics in Medicinal Chemistry, 17: 1843-1857 (2017).

* cited by examiner a)

b)

a)

b)

GANGLIOSIDE GM3-CONTAINING NANOPARTICLES AS IMMUNOMODULATORS

CROSS-REFERENCE TO RELATED APPLICATIONS

This application is the U.S. national phase of International Patent Application No. PCT/CU2018/050005, filed on 17 Dec. 2018, which claims the benefit of priority to Cuban Patent Application Serial No. CU 2017-0173, filed on 27 Dec. 2017; the entire contents of each of said applications are incorporated herein in their entirety by this reference.

The present invention relates to the fields of immuno-nanotechnology and immuno-oncology, especially to immunomodulators for the treatment of individuals with cancer and/or chronic infections. It particularly describes a nano-particulate immunomodulator specialized in interfering specifically with Myeloid-derived suppressor cells (MDSCs) (MDSC) in these individuals and also restoring the T cell response.

BACKGROUND

Recently, important clinical results have been obtained with the use of immune checkpoint inhibitory antibodies (Abs), with the capacity to induce long-term objective responses with a significant impact on patient survival. These treatments, which modulate the immune system and restore the patient's capacity to destroy tumor cells, have led to the rebirth of cancer immunotherapy with a special focus on the design of new immunomodulators.

However, there are other suppressor circuits of the anti-tumor immune response, which are important targets for the development of new immunomodulators (Malmberg K. J. et al (2004) Cancer Immunol Immunother 53 (10): 879-92). Myeloid-derived suppressor cells (MDSCs) constitute one of the main cell populations mobilized by tumors with the capacity to suppress the immune response (Mantovani A. et al. (2010) Curr Opin Immunol 22 (2): 231-7; Condamine T. et al (2011) Trends Immunol 32 (1): 19-25). Particularly, as proposed by Shipp et al. in a review article, the frequency of circulating MDSCs is a factor of poor prognosis in patients with tumors from a wide variety of locations. In addition, high circulating levels of these populations are associated with a lower benefit of conventional therapies such as chemotherapy, radiotherapy and even anti-checkpoint Abs (Shipp C. et al. (2016) Cell Mol Life Sci 73(21): 4043-61). In humans, as a general consensus, three populations of MDSCs are described: the early stage MDSCs (eMDSC), defined as $LIN^-$ $CD11b^+CD33^+HLA-DR^-$; monocytic MDSCs (mMDSC), defined as $CD14^+HLA-DR^{low/-}/-$ and granulocytic MDSCs (gMDSC), with $CD11b^+CD33^+CD14^-$ $CD15^+$ ($CD66b^+$) phenotype (Bronte V. et al (2016) Nat Commun 7: 12150). All three populations are considered to be suppressors of the tumor-specific immune response (Shipp C. et al (2016) Cell Mol Life, Sci 73 (21): 4043-61).

The research strategies being currently developed to counteract the immunosuppression induced by the MDSCs are focused on three approaches: (1) reduce their number, (2) affect their function and (3) influence their differentiation. In these directions, encouraging results have already been reported with several of the drugs evaluated (Najjar Y. G. et al (2013) Frontiers in Oncology 3 (49): 1-9).

Particularly relevant to the present invention within the therapeutic strategies targeting the MDSCs, are strategies based on nano-particulate systems. It is known that nanoparticles offer a wide range of applications and that depending on the size and surface characteristics, they behave differently in vivo. Size, for example, conditions the drainage site and surface characteristics influence adhesion and capture mechanisms (Wilkerson A. et al (2017) Current Topics in Medicinal Chemistry 17: 1843-57). In this sense, as reported by Serda R. E., particulate systems with diameters in the range of 500-2000 nm are preferentially captured at the injection site and moved to the lymph nodes (LN), while particles with diameters between 20 and 200 nm passively drain to the LNs where they interact with the resident cells (Serda R. E. (2013) Int J of Nanomed 8:1683-1696).

To date, only six nano-particle-based strategies with effect on MDSCs have been described, among which are: nano-particles loaded with gemcitabine, nano-particles loaded with chemokine CCL21, nano-particles loaded with CpG, liposomes loaded with all-trans retinoic acid and nano-particles engineered with glucans (Wilkerson A. et al (2017) Current Topics in Medicinal Chemistry 17:1843-57). These five strategies share three fundamental characteristics: the size of the nano-particles is comprised within the range from 30 to 250 nm, their use is restricted to murine models and they constitute particles without per se effect on the MDSCs, but they are carrier systems of the biological agent.

The sixth strategy based on nano-particulate systems with effect on the MDSCs is the use of very small proteoliposomes (VSSP) that contain the GM3 ganglioside. These preparations can be considered as the technical solution closest to the present invention. Initially, Molina et al, in U.S. Pat. No. 8,591,917 B2, describe a method for stimulating the immune response in subjects using the VSSP administered subcutaneously (SC). Additionally, the studies of Fernandez et al. and Oliver et al. demonstrated that in healthy, tumor-bearing mice or mice with chemotherapy-induced leukopenia, the administration of VSSP induces in the spleen a significant increase of cells with a phenotype similar to that of MDSCs but with a suppressive capacity markedly diminished (Fernandez A. et al. (2011) J Immunol 186: 264-74; Oliver L. et al (2012) Vaccine 30: 2963-72). Other studies also describe that the use of VSSP in tumor-bearing mice prevents the cross-presentation of antigens by the MDSCs induced by the tumor and induces their differentiation into antigen presenting cells (Fernandez A. et al (2014) J ImmunoTherapy of Cancer 2:5). The way to obtain these VSSPs is described by Rodriguez et al. in U.S. Pat. No. 6,149,921, emphasizing that the conjugation of the *Neisseria meningitidis* proteins is mixed with an excess of ganglioside GM3 in the presence of a detergent, which is then eliminated by a dialysis method. Additionally, Estevez et al. describe that after dialysis, an ultra-centrifugation process that discards conjugates with greater mass and size occurs (Estevez F. et al (2000) Vaccine 18: 190-7).

The novel active principle of the immunomodulatory preparation described in the present invention, also includes conjugates of *N. meningitidis* membrane vesicles and GM3 ganglioside. This preparation has particular characteristics of size, surface charge and a morphology associated with nano-particulate systems which has never before been described in any technical solution or previous scientific publication. These characteristics provide this new invention with advantageous and surprising properties in terms of their effect on the MDSCs, as compared to those previously described by Fernández A. et al. and Oliver L. et al. The present invention, being preferably administered by SC for the treatment of patients with tumors, and contrary to what the prior art teaches, induces a convenient and significant decrease of the gMDSCs and the mMDSCs, and has an impact on the response of T lymphocytes and the survival of treated patients. Therefore, the novelty of the present invention consists of providing a new immunomodulator with effect in the decrease of MDSCs levels in patients with tumors.

BRIEF DESCRIPTION OF THE INVENTION

One embodiment of the present invention is a pharmaceutical composition for immunomodulating the immune response in cancer patients comprising nanoparticles formed by hydrophobic conjugation of the outer membrane protein complex (OMPC) of the *N. meningitidis* bacterium to GM3 ganglioside, where the protein-ganglioside conjugation ratio ranges from 1.5:1 to 10:1.

Particularly, said composition is characterized by a monomodal distribution of size in the range between 15-25 nm particle size, polydispersity index of 0.230, negative Z potential with nominal value in the range between 25-45 mV.

In a particular embodiment, the present invention relates to the use of the pharmaceutical composition object of the present invention in the treatment of cancer, and particularly as an immunomodulator of MDSCs in patients with cancers that increase the presence of these cells.

In another embodiment, the present invention relates to a method of treating a subject in need thereof comprising administering the pharmaceutical composition described in the present invention by SC route, intradermally, intramuscularly, intratumorally or by direct application to mucosal membranes with a weekly frequency for at least a total of four doses and then in fortnightly or monthly maintenance doses for at least six months.

In a particular embodiment, the object of the present invention is a method of selecting patients with cancer as candidates for receiving the treatment with the described pharmaceutical composition, which involves:

the extraction of a sample of blood and/or tumor tissue from the patient and the determination of the levels of MDSCs in said sample of blood and/or tumor tissue.

Patients who have a high frequency or high absolute number of MDSCs in blood or those who tested positive in terms of degree of infiltration of MDSCs in the tumor tissue will be considered candidates for such treatment.

DETAILED DESCRIPTION OF THE INVENTION

Immunomodulatory Composition

The present invention provides an immunomodulatory system that significantly decreases circulating MDSCs in those patients with cancer who have high levels of these cells circulating or in the tumor. An immunomodulatory system can be defined as one capable of eliminating or modulating any of the suppressive mediators of the immune response, as is the case of the MDSCs.

The immunomodulatory object claimed in the present invention consists of nano-particles obtained from the outer membrane of the Gram-negative bacterium, *N. meningitidis* associated to the GM3 ganglioside. This invention establishes that the OMPC of *N. meningitidis* is first dispersed in a Tris-HCl buffer solution containing a mixture of sodium deoxycholate (10-40 mM) and sodium dodecyl sulfate (1-10 mM) in a stirred reactor for a period of time ranging from 1 to 36 hours.

Next, a mass of GM3 ganglioside from 0.6 to 10 times less than the added mass of OMPC is added, so that the protein:ganglioside ratio is from 1.5:1 to 10:1 and agitation is prolonged. The formation of nano-particles is achieved through the use of a tangential filtration system with membranes from 10 kDa to 100 kDa and at a transmembrane pressure of from 1.15 to 1.75 bar, so that the detergents are totally removed. The ultrafiltered remnant solution is ultracentrifuged at 100000 g and concentrated to adjust its concentration to the desired dosage from 0.1 to 2 mg/ml of OMPC and sterilized by filtration in a sterile 0.2 μm pore size capsule.

With the conjugation of a ratio of protein mass and ganglioside favorable to the amount of protein and the process of tangential ultrafiltration under controlled conditions, a preparation with defined characteristics that we named VSSP-iMod is obtained. The analysis of morphology, size and superficial charge density the particles shows the presence of a heterogeneous, nano-particulate formulation, from 15 to 25 nm in size and with a negative Z potential of nominal value ranging from 25 to 45 mV.

Methods of Identification and/or Selection of Patients for Treatment with VSSP-iMod For the selection of patients to whom the VSSP-iMod will be administered, the level of gMDSCs and mMDSCs that could suppress the T-specific response to tumors is determined. An increase in MDSCs due to the presence of a tumor can be determined by the evaluation of the different subpopulations of these cells in circulation or in the tumor microenvironment. In addition, its presence implies the increase of certain plasma proteins and circulating DNA. The sources of the samples for evaluation include both peripheral blood and tumor samples that include but are not limited to tumor biopsies, circulating plasma proteins, ascites fluid, and circulating DNA.

The increase in these cells can be determined by a diagnostic or prognostic assay using flow cytometry, immunohistochemistry (IHC), ELISA, immunofluorescence or polymerase chain reaction. On the other hand, a patient, who has no increased MDSC levels due to its stage or tumor location, is the one that has higher levels than those of normal healthy donors but who does not reach the considerable levels observed in patients with the same pathology.

The determination of the levels of MDSCs in the blood samples of the patients is carried out by flow cytometry, where both populations are analyzed within the $FSC^{intermediate/high}/SSC^{low/high}$ region. In particular, for the gMDSC population, the double-positive population for CD11b and CD33 is selected and within it, the subpopulation positive for CD66b and negative for CD14. For the mMDSCs, the population with negative or low expression of HLA-DR and positive for CD14 is selected. Based on these results, and related to the same determination for healthy donors matched by age and gender, the levels of MDSCs can be classified as follows, according to their frequency or absolute number:

Negative: Values of percentage and/or number in the range determined by the mean of the normal values (M)+/−the standard deviation with 95% confidence.

Weak: Values of percentage and/or number 2M≤MDSC<3M with respect to M.

High: Values of percentage and/or number with values 3M≤MDSC.

Patients with high frequency or absolute number of MDSCs in blood will be treated with VSSP-iMod.

To determine the levels of MDSCs in the samples of tumor tissues, measurement by IHC techniques of the CD33+ cells can be used. To this purpose, the percentage of CD33+ cells in the tissue must be determined and is expressed as follows:

Negative: Less than 10% of positive cells

Positive/Low infiltrate MDSCs: Between 10-19% of positive cells

Positive/High infiltrate MDSCs: More than 20% positive cells Depending on its histological type and stage, it can be considered that a tumor recruits MDSCs provided that it is positive as to its degree of infiltration by CD33+ cells.

Therapeutic Application and Treatment Methods

The present invention provides an immunomodulatory composition specialized in decreasing the MDSCs both of gMDSC and mMDSC phenotypes, which establishes a solution of peculiar interest for immuno-oncology, where it is known that MDSCs constitute an essential suppressor node of the antitumor immune response.

The progression of certain tumors is accompanied by the recruitment to the tumor site of the MDSCs, for which specialized mechanisms have been described of suppressing the antitumor immune response of T and NK lymphocytes. This invention proposes that in those patients, who have elevated gMDSC and/or mMDSC, in circulation and/or in the tumor, the number of these cells can be significantly reduced by treatment with VSSP-iMod. This reduction will allow in these patients for the natural antitumor immune response or that induced by some therapy not to be suppressed by the MDSCs, which will translate into the survival of the treated patients.

The VSSP-iMod immunomodulator of the present invention can be introduced into the patient by: SC, intradermal, intramuscular, intratumoral route or by direct application on the mucosal membranes.

Among the types of cancer that can be treated with the VSSP-iMod immunomodulator object of the present invention are those for which it has been reported that they recruit MDSCs as immunosuppressive mechanism of the antitumor immune response. More particularly, examples of these cancers include melanoma, prostate cancer, head and neck, ovary, bladder, hepatocellular carcinoma, non-small cell lung cancer, chronic lymphocytic leukemia, squamous cell carcinoma of the esophagus, Hodgkin's lymphoma, renal carcinoma and mammary carcinoma.

The dose range of the VSSP-iMod immunomodulator to be used in humans is from 100 μg to 2 mg, preferably from 200 μg to 1200 μg (according to OMPC content).

Said immunomodulator is administered in the subjects with a weekly frequency during at least a total of four doses so as to achieve a rapid decrease of MDSCs and subsequently in fortnightly or monthly maintenance doses for at least six months. This treatment can be administered chronically for as long as the patient requires it.

The present invention is further elaborated with the following examples and drawings. However, these examples should not be construed as limiting the scope of the invention. In these examples experimental details that allow to verify the particular physico-chemical characteristics of the VSSP-iMod and its effectiveness on the reduction, in treated patients, of the MDSCs content are included. In addition, the examples show about the impact of this decrease on the T lymphocytes response as well as on the survival of treated patients.

EXAMPLES

Example 1. The VSSP-iMod has a Defined Size and Surface Charge

Figure 1:
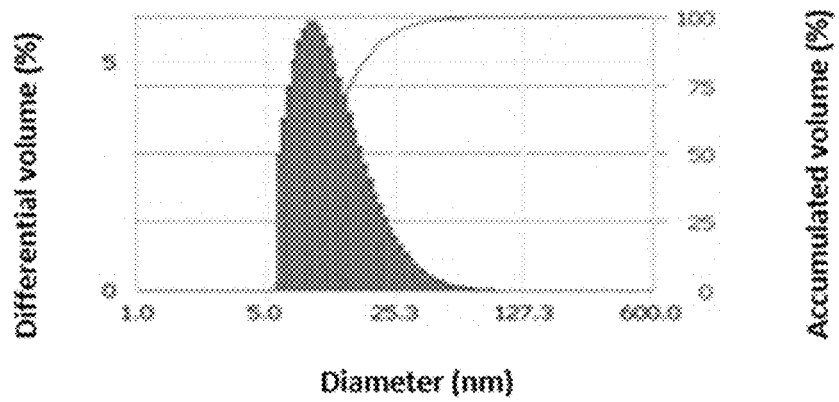
FIG. 1. Evaluation by Photonic Correlation Spectroscopy of the diameter of VSSP-iMod particles.
Figure 2:
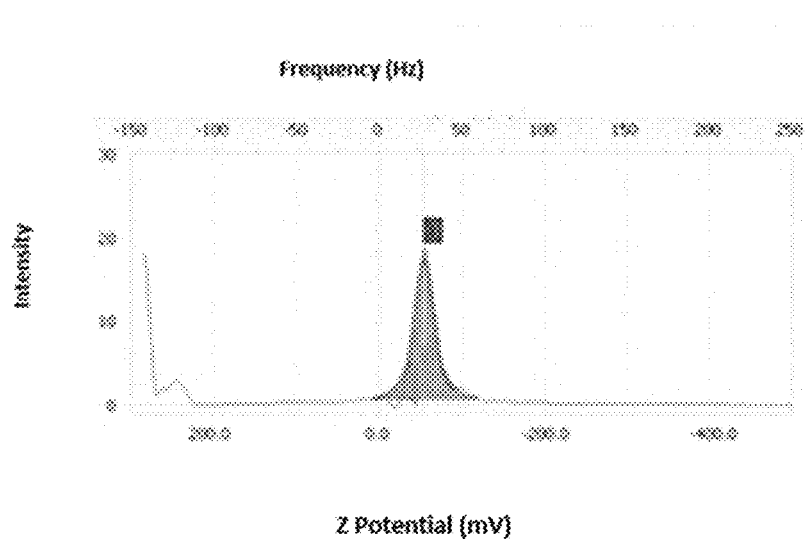
FIG. 2. Evaluation by Photonic Correlation Spectroscopy of Z Potential of VSSP-iMod particles.

The size in nanometers and Z potential of the particles that make up the VSSP-iMod were measured by Photonic Correlation Spectroscopy. Samples were evaluated in triplicate, size and potential Z values were obtained using the CONTIN and Smoluchowski algorithms respectively. As shown in FIG. 1, the VSSP-iMod showed a monomodal distribution in a range from 15 to 25 nm in volume distribution, with a polydispersity index (PDI) of 0.230, which means that we are in the presence of a heterogeneous formulation of particles. Additionally, the VSSP-iMod showed a negative Z potential and its nominal value was in the range between 25-45 mV as shown in FIG. 2.

Example 2. Nano-Particulate Morphology of VSSP-iMod

Figure 3:
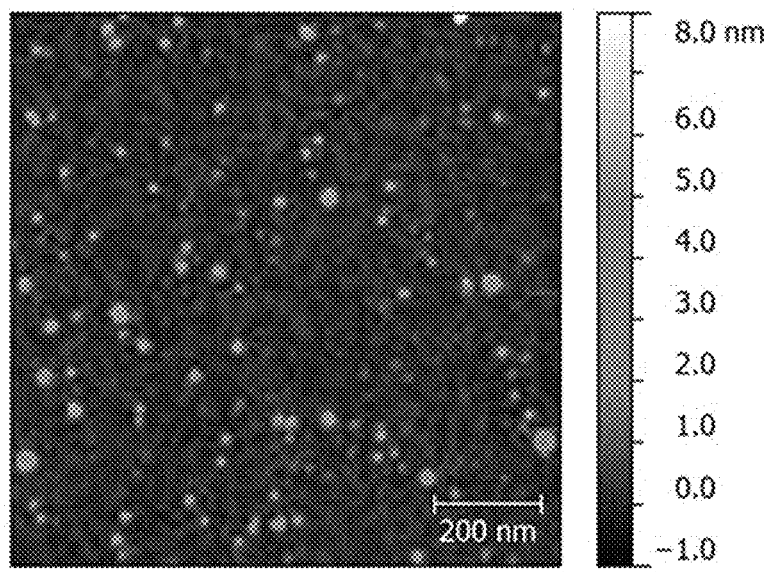
FIG. 3. Image of the Morphology of VSSP-iMod particles by Atomic Force Microscopy.

The images of the VSSP-iMod were obtained in a Multimode Microscope of Atomic Force and a silicon cantilever was used. 50λ of sample were applied to a mica previously functionalized with a 50 mol/L nickel chloride solution. A 1/10 dilution with Tris buffer solution 10 mmol/L pH 8.5 was performed to the VSSP-iMod, prior to the application to the mica. The image of FIG. 3 shows a heterogeneous formulation composed of nano-particulate structures of spherical nature in the order of tens of nanometers, which is in total correspondence with the result obtained by Photon Correlation Spectroscopy.

Figure 4:
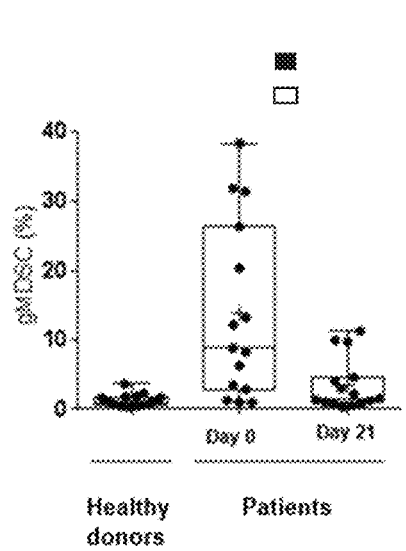
FIG. 4. Evaluation by flow cytometry of the effect of treatment with VSSP-iMod in patients with metastatic renal cell carcinoma (mRCC) of a) the frequency of gMDSCs and b) percentage of patients with frequency of gMDSCs above and below the median.
Figure 4:
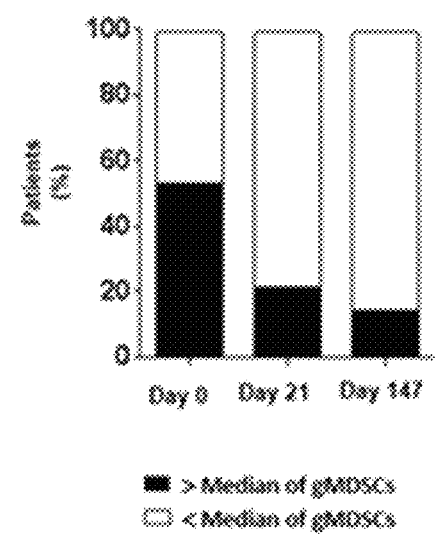

Example 3. VSSP Decreases the Frequency and Suppressive Activity of MDSCs in Patients with mRCC The effect of VSSP-iMod on MDSCs in patients with mRCC was evaluated. To this purpose, fifteen patients with this diagnosis were treated with 400 μg of VSSP-iMod administered by SC route in the deltoid region. A total of four doses of VSSP-iMod were administered with a weekly frequency followed by a monthly maintenance doses until completing 6 months of treatment. In this assay the frequency of gMDSCs was evaluated by flow cytometry. To this purpose, a total of 200,000 cells were analyzed and the percentages of gMDSCs were determined by measuring the CD11b+/CD66b+/CD14− phenotype within the total PBMC. As a control, the frequency of gMDSCs in 15 healthy donors matched by age and gender was evaluated. As seen in FIG. 4a, the VSSP-iMod decreased the frequency of circulating gMDSCs in patients after 21 days or three doses after treatment initiation. The state of the art teaches that patients who present gMDSCs below the median established for patients of a certain location, have a significantly higher survival than those who have levels below it (Shipp C. et al (2016) Cell, Mol. Life, Sci. 73 (21): 4043-61). The analysis of the percentage of patients with gMDSC frequency above and below the median is shown in FIG. 4b. As can be observed after treatment with VSSP-iMod, only about 20% of the treated patients keep the MDSCs high. This result was maintained on day 147 or after the fifth month, which indicates that this effect of VSSP-iMod is maintained throughout the treatment.

Figure 5:
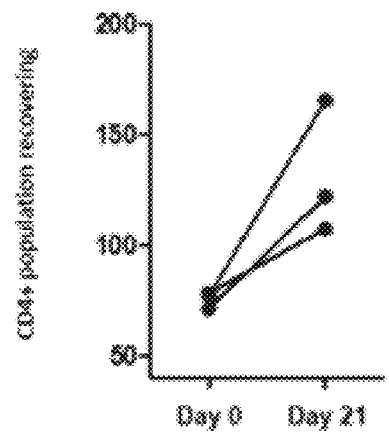
FIG. 5. Evaluation by flow cytometry of the effect of the treatment with VSSP-iMod on the capacity of the MDSCs to suppress the proliferation of: a) TCD4+lymphocytes and b) TCD8+lymphocytes.
Figure 5:
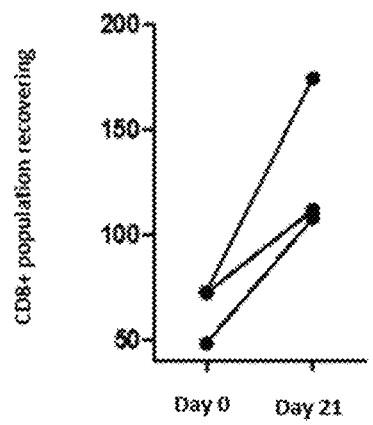

In these patients, the consequences for the response of lymphocytes of the effect of VSSP-iMod on the MDSCs was also evaluated in a proliferation experiment by flow cytometry. A total of $40 \times 10^6$ cells from the PBMC of said patients were used as starting material. The CD11b+ cells were purified by the use of magnetic beads conjugated to a CD11b specific Ab. The CD11b− negative fraction was labeled with CFSE and cultured alone or with CD11b+ cells at a 5:1 ratio for 96 hours. FIG. 5 shows the relative proliferation percentage of T lymphocytes on day 0 and on day 21 after the administration of VSSP-iMod in RCC patients. As seen in FIG. 5a, the proliferation of TCD4+lymphocytes increases on day 21, an effect similar to that observed in TCD8+ lymphocytes (FIG. 5b), which means that the VSSP-iMod is able to modulate the MDSCs-mediated suppression of T cell proliferation in the RCC patients.

The majority of the patients enrolled in the trial showed good quality of life at the end of their treatment, as established in the protocol, it was decided that they continue with monthly immunizations. Treatment prolongation maintained the gMDSCs below the median at day zero and the survival median of the total patients in this trial was 37.5 months (Table 1). This value is much higher than the historical median of 6.6 months reported for similar patients treated with interferon, which is the current standard of treatment in Cuba. Additionally, the clinical practice guidelines for mRCC of the National Comprehensive Cancer Network (NCCN) classify patients according to the models of the Memorial Sloan Kettering Cancer Center (MSKCC) as having favorable, intermediate and poor prognosis. These guidelines state that patients with mRCC treated with therapies against the vascular endothelial growth factor have a median survival of 27 months in the case of those diagnosed as having intermediate prognosis, while 75% of those diagnosed as having a favorable prognosis are alive at 24 months. The relative comparison of the values stated in the guidelines against those obtained with VSSP-iMod, indicates that the effect of VSSP-iMod on the gMDSCs also produced a survival higher than the standard formed in the NCCN guidelines. In the VSSP-iMod trial, 100% of patients with favorable prognosis were alive at 36 months and those with an intermediate prognosis had a median survival of 42 months.

TABLE 1

Survival of mRCC patients treated with VSSP-iMod.

| Patient | Total number of doses received | Survival from inclusion in trial (months) | Prognosis according to MSKCC at inclusion |
|---|---|---|---|
| RCC 01 | 38 | 64.47 | Favorable |
| RCC 02 | 8 | 5.2 | Poor |
| RCC 03 | 38 | 64.47 | Intermediate |
| RCC 04 | 5 | 2.57 | Poor |
| RCC 05 | 8 | 30.07 | Intermediate |
| RCC 06 | 12 | 37 | Intermediate |
| RCC 07 | 2 | 5.9 | Poor |
| RCC 08 | 16 | 59.37 | Intermediate |
| RCC 09 | 16 | 54.07 | Favorable |
| RCC 10 | 37 | 48 | Intermediate |
| RCC 11 | 16 | 43.6 | Favorable |
| RCC 12 | 41 | 36.5 | Favorable |
| RCC 13 | 24 | 36.5 | Intermediate |
| RCC 14 | 4 | 2.17 | Poor |
| RCC 15 | 12 | 10.3 | Poor |

Figure 6A:
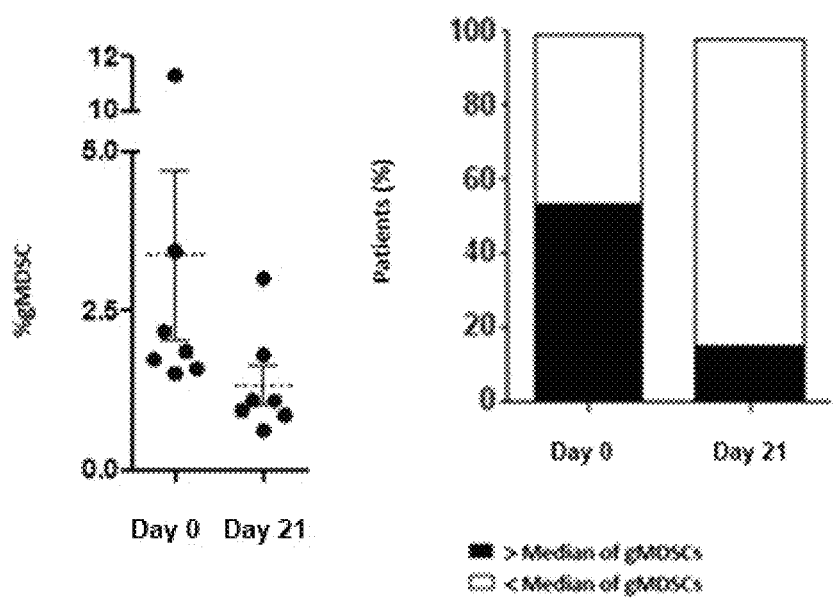
FIG. 6. Flow cytometric evaluation in patients with mammary carcinoma of the effect of treatment with VSSP-iMod on: a) frequency and % of patients with gMDSC frequency above and below the median, b) frequency and % of patients with mMDSC frequency above and below the median.
Figure 6B:
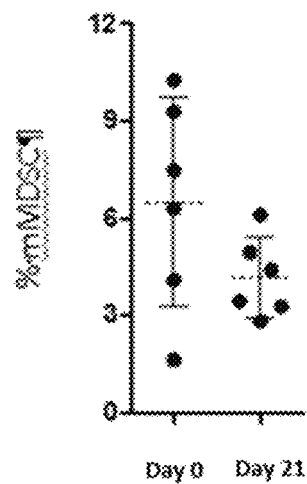
Figure 7:
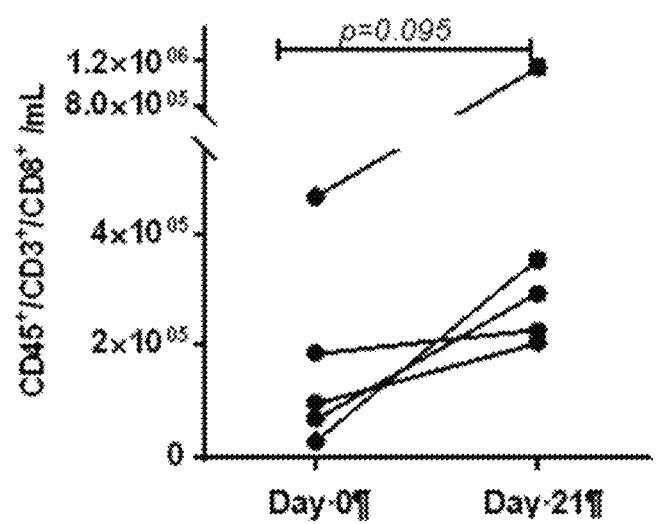
FIG. 7. Determination by flow cytometry of the effect of treatment with VSSP-iMod on the absolute number of TCD8+lymphocytes in patients with mammary carcinoma.

Example 4. VSSP Decreases the Frequency of MDSCs of Monocytic and Granulocytic Phenotype in Patients with Breast Carcinoma The effect of VSSP-iMod on MDSCs was also evaluated in patients with breast carcinoma. To this purpose, a Phase 0 Window-of-Opportunity trial was designed, in which patients received 400 μg of VSSP-iMod with a weekly frequency for three weeks by SC route in the deltoid region. This treatment was administered in the conventional time established between the diagnosis and the start of the standard treatment of surgery or chemotherapy indicated by the physician. In this trial the frequency of G-MDSCs, mMDSCs and CD8 T cells was determined by flow cytometry. A total of 200,000 cells were analyzed and the percentages of gMDSCs and mMDSCs were determined using the phenotypes CD11b+/CD66b+/CD14y CD11b+/CD14+/HLA-DR$^{low/neg}$, within the total of PBMC, respectively. As seen in FIG. 6a, the VSSP-iMod decreased the frequency of circulating gMDSCs and this same behavior was observed in the mMDSCs (FIG. 6b) circulating in the patients, after 21 days of treatment. Additionally, the analysis of the percentage of patients with frequency of gMDSCs and mMDSCs above and below the median shows that, after treatment with VSSP-iMod, only 15% and 0% of treated patients maintained the gMDSCs and mMDSCs high respectively. This treatment also increased the frequency of CD8+ T cells in the blood of patients (FIG. 7).

The invention claimed is:

1. A pharmaceutical composition comprising nanoparticles characterized by hydrophobic conjugation of outer membrane protein complex (OMPC) of *Neisseria meningitidis* bacterium to a GM3 ganglioside, wherein the OMPC: GM3 ganglioside conjugation ratio ranges from 1.5: 1 to 10: 1.

2. The composition of claim 1, wherein the nanoparticles are characterized by a monomodal distribution of volume in a range from 15 to 25 nm particle size, polydispersity index of 0.230, and/or negative Z potential with nominal value in the range from 25 to 45 mV.

3. A method for treating a subject in need thereof comprising the administration of the pharmaceutical composition according to claim 1 by SC, intradermal, intramuscular, intratumoral routes or by direct application to mucosal surfaces with a weekly frequency for at least a total of four doses and subsequently fortnightly or monthly in maintenance doses for at least six months.

4. A pharmaceutical composition comprising nanoparticles, wherein each nanoparticle comprises outer membrane protein complex (OMPC) of Neisseria meningitidis bacterium hydrophobically conjugated to a GM3 ganglioside, wherein the protein-ganglioside conjugation ratio ranges from 1.5: 1 to 10: 1, and wherein the composition is characterized by a monomodal distribution of volume in a range from 15 to 25 nm particle size, polydispersity index of 0.230, negative Z potential with nominal value in the range from 25 to 45 mV.

5. A pharmaceutical composition comprising nanoparticles characterized by hydrophobic conjugation of outer membrane protein complex (OMPC) of Neisseria meningitidis bacterium to a GM3 ganglioside, wherein the nanoparticles are characterized by a monomodal distribution of volume in a range from 15 to 25 nm particle size, a polydispersity index of 0.230, and a negative Z potential with nominal value in the range from 25 to 45 mV.

6. A method of producing a nanoparticle, the method comprising conjugating outer membrane protein complex (OMPC) of Neisseria meningitidis bacterium to a GM3 ganglioside, where the OMPC:GM3 ganglioside conjugation ratio ranges from 1.5:1 to 10:1.

\* \* \* \* \*